(12) United States Patent
Ghetta et al.

(10) Patent No.: US 12,328,808 B2
(45) Date of Patent: Jun. 10, 2025

(54) LIQUID TARGETS FOR THE PRODUCTION OF NUCLEAR PARTICLES

(71) Applicants: Centre National de la Recherche Scientifique, Paris (FR); INSTITUT POLYTECHNIQUE DE GRENOBLE, Grenoble (FR); UNIVERSITE GRENOBLE ALPES, Saint-Martin-d'Heres (FR)

(72) Inventors: Véronique Ghetta, Sechilienne (FR); Julien Giraud, Le Pont de Claix (FR); Daniel Santos, Biviers (FR)

(73) Assignees: CENTRE NATIONAL DE LA RECHERCHE SCIENTIFIQUE, Paris (FR); INSTITUT POLYTECHNIQUE DE GRENOBLE, Grenoble (FR); UNIVERSITE GRENOBLE ALPES, Saint-Marlin-d'Heres (FR)

( * ) Notice: Subject to any disclaimer, the term of this patent is extended or adjusted under 35 U.S.C. 154(b) by 611 days.

(21) Appl. No.: 17/596,613

(22) PCT Filed: Jun. 8, 2020

(86) PCT No.: PCT/EP2020/065875
§ 371 (c)(1),
(2) Date: Jan. 25, 2022

(87) PCT Pub. No.: WO2020/249524
PCT Pub. Date: Dec. 17, 2020

(65) Prior Publication Data
US 2022/0304135 A1    Sep. 22, 2022

(30) Foreign Application Priority Data
Jun. 14, 2019 (FR) .................................. 1906353

(51) Int. Cl.
*H05H 6/00* (2006.01)
*G21G 4/02* (2006.01)
*H05H 3/06* (2006.01)

(52) U.S. Cl.
CPC .............. *H05H 6/00* (2013.01); *G21G 4/02* (2013.01); *H05H 3/06* (2013.01); *H05H 2006/007* (2013.01)

(58) Field of Classification Search
CPC .............. H05H 6/00; H05H 3/06; G21G 4/02
See application file for complete search history.

(56) References Cited

U.S. PATENT DOCUMENTS

| 3,733,490 A | * | 5/1973 | Roche | ...................... H05H 6/00 376/151 |
| 3,993,910 A | * | 11/1976 | Parkin | ..................... H05H 6/00 376/199 |

(Continued)

FOREIGN PATENT DOCUMENTS

| CN | 104853515 A | 8/2015 |
| CN | 109257864 A | 1/2019 |

OTHER PUBLICATIONS

M. S. Avilov et al. "Project of Proton Accelerator Based Traget for Neutron Production" Proceedings of the Second Asian Particle Accelerator Conference; Jan. 1, 2001 (3 pages).

(Continued)

*Primary Examiner* — Sharon M Davis
(74) *Attorney, Agent, or Firm* — Maier & Maier, PLLC

(57) ABSTRACT

According to one aspect, the present description concerns a target (20) for the production of nuclear particles. The target comprises a shell (24) formed by a surface of revolution and mounted in rotation about an axis of rotation (21) that coincides with an axis of revolution of the shell. The target further comprises a reservoir comprising a target material in the liquid state during use, the target material being suitable for producing the nuclear particles; a target material raising device configured to entrain, in operation, the target material from the reservoir toward an upper surface (244) of the shell; a gutter formed along an external perimeter (245) of the shell and configured to receive, in operation, droplets derived from a film (22) of target material induced by centrifugal action on said upper surface of the shell as the shell is rotated; at least one return pipe forming a fluid connection between the gutter and the container; an inlet pipe configured, in operation, to let in a beam of accelerated particles into a zone of impingement of said accelerated particles with the shell, said zone of impingement being situated on said upper surface of the shell, the interaction of said accelerated particles with the target material circulating on said upper surface of the shell generating said nuclear particles.

7 Claims, 4 Drawing Sheets

(56) References Cited

U.S. PATENT DOCUMENTS 5,392,319 A * 2/1995 Eggers .................... H05H 3/06
                                              376/151
5,870,447 A * 2/1999 Powell .................... G21G 1/10
                                              376/190

OTHER PUBLICATIONS

International Search Report issued in International Application No. PCT/EP2020/065875, mailed Sep. 9, 2020 (7 pages).
Written Opinion issued in International Application No. PCT/EP2020/065875; Dated Sep. 9, 2020 (13 pages).

* cited by examiner

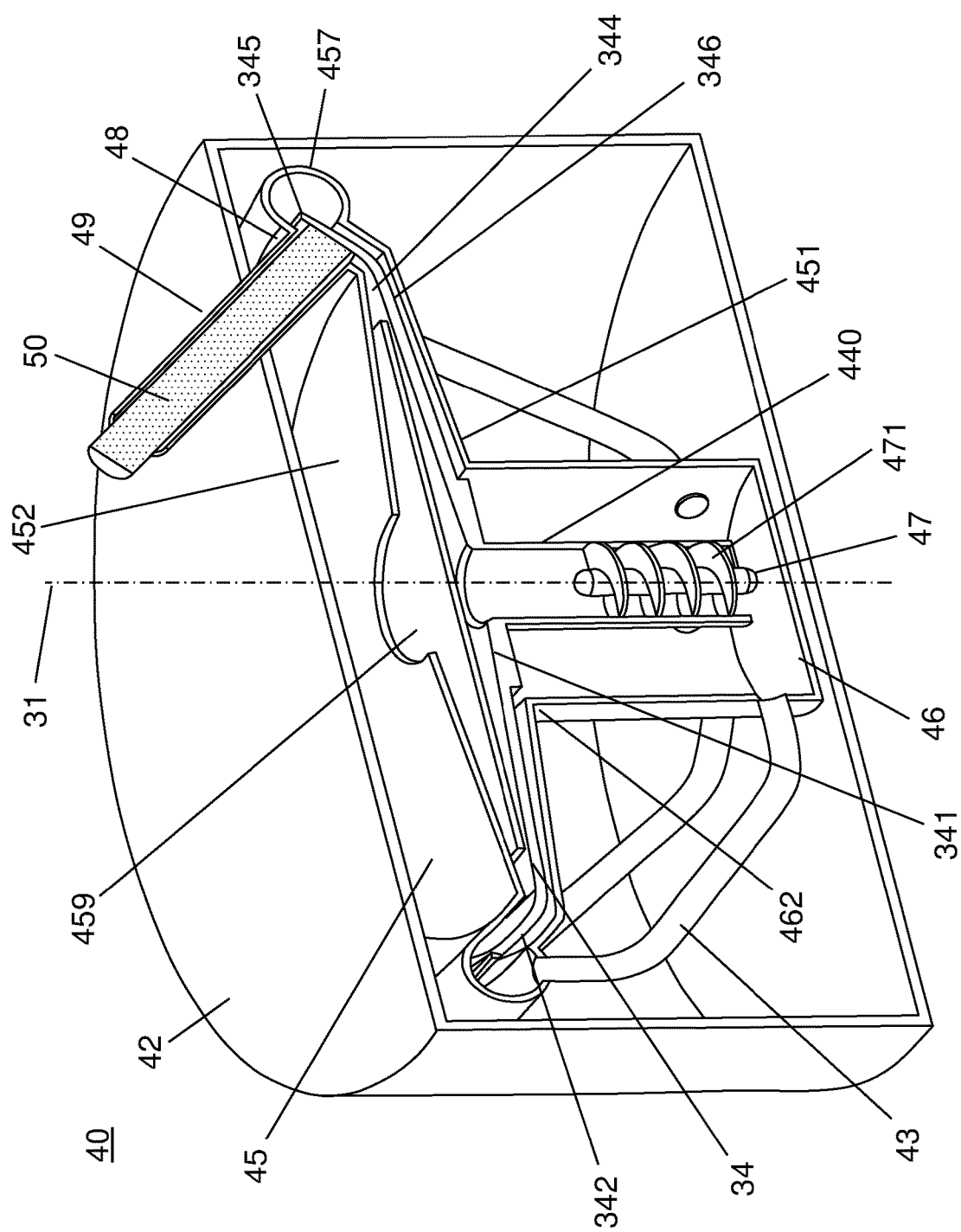

LIQUID TARGETS FOR THE PRODUCTION OF NUCLEAR PARTICLES

TECHNICAL FIELD OF THE INVENTION

The present invention relates to liquid targets for the production of nuclear particles and to systems incorporating such targets. It notably relates to targets for the generation of neutron fields.

PRIOR ART

Nuclear particles (for example neutrons, protons, alpha particles) are able to be produced through a specific nuclear reaction resulting from the interaction of a beam of incident particles (for example protons, deuterons or other atomic nuclei) the production of which is already known, on targets formed by a material that allows the specific nuclear reaction.

In particular, the production of high-flux neutron fields (namely fields with flux in excess of $10^{12}$ n·cm$^{-2}$·s$^{-1}$) finds applications in very varied fields, such as, for example, in the non-destructive testing and analysis of materials, the doping of silicon for power electronics and the field of medicine. In the field of medicine, there is particular interest in the application known as BNCT (which stands for Boron Neutron Capture Therapy), namely a therapy whereby neutrons are captured by boron 10 ($^{10}$B) previously vectorized onto the tumor. In this application, neutron energies comprised between around 0.5 eV and 10 keV are favored for irradiating the patient.

The nuclear reaction $^{7}$Li(p,n)$^{7}$Be of protons with energy E>1.88 MeV with lithium used as a target material is known notably for the production of neutron fields. In this reaction, a proton (or a deuteron) is collided with a lithium ($^{7}$Li) nucleus to form a beryllium ($^{7}$Be) nucleus with the ejection of a neutron of energy comprised between 25 keV and 785 keV. A moderator is then used to reduce the energy of the neutrons. The $^{7}$Be nucleus formed in the nuclear reaction is unstable, with a half-life of 53 days; it decays by electron capture, emitting a 478 keV gamma ray, which is harmful from a radio protection standpoint. There is therefore a desire to control the amount of $^{7}$Be present in the target.

The depth of penetration into the target material can vary according to the energies of the incident beams of particles employed. In the case of low energies, this penetration is low and the transfer of energy from the beam occurs at the subsurface, creating significant heating of the target material. There is therefore a benefit in working with thin target materials in order to spread some of the heat supplied by the beam of incident particles into the target material. Because solid thin layers have problems of stability and deterioration under the effect of the beam, "liquid" targets represent an attractive solution for high current intensity beams.

Thus, the $^{7}$Li(p,n)$^{7}$Be reaction described above can be obtained using a target based on solid lithium. Such a target comprises a fine layer of solid lithium arranged on a support and which is struck by a beam of particles emanating from a particle accelerator. In practice, the integrity of the layer and its adhesion to the support need to be guaranteed by the continuous removal of a thermal power in excess of 3 kW/cm$^{2}$. As lithium has a low melting point (180.5° C.) the life of a target based on solid lithium is limited over time and the target therefore has to be changed very regularly. Targets based on liquid lithium have also been developed. Liquid lithium is able to withstand higher temperatures compared with solid lithium. As a result, compared with a target based on solid lithium, the problems associated with the integrity of the layer, its adhesion to the support and keeping it at a very low temperature (<180° C.) are solved.

Examples of targets based on liquid lithium are described notably in Halfon et al. [Ref 1] and Kobayashi et al. [Ref 2]. The targets based on liquid lithium that are described in the aforementioned reference works involve circulating liquid lithium in closed pipe with, at the particle beam inlet, an open and curved zone on which the lithium forms a film ranging from several hundred microns up to 1.5 mm in thickness. The flow rate of lithium in the pipe is high enough to establish a high-speed flow of the thin film of liquid past the beam (7 m/s in the case of the target disclosed in [Ref 1], up to 30 m/s in the case of the target disclosed in [Ref 2]), so that the temperature of the film remains acceptable for limiting the evaporation of the lithium.

As explained previously, the $^{7}$Be produced by the $^{7}$Li(p,n)$^{7}$Be reaction contributes to creating a not-insignificant quantity of a radioactive species ($^{7}$Be); it then follows that there is a possibility of activation of the materials of the circuit containing the circulating lithium. One solution for overcoming the problems of the radiotoxicity of the $^{7}$Be produced, and which is described for example in [Ref 1] is to use a cold trap at the lithium reservoir in order to condense the $^{7}$Be to the solid state in the reservoir. This configuration entails protecting the reservoir more particularly from a radiological viewpoint.

Thus, although it does allow the generation of a neutron field suited to BNCT use, the use of liquid lithium in the circulating targets described in the prior art is, in practice, limited by the quantity of liquid lithium required and the bulkiness of the installation, made more complex by the need to manage the radiotoxicity associated with the $^{7}$Be.

Patent U.S. Pat. No. 5,870,447 [Ref 3] describes a target comprising a rotating disk and a circuit for liquid lithium which is recirculated by means of a pump, allowing liquid lithium to be sprayed in the form of droplets by centrifugal force from the center toward the periphery of the disk. In one embodiment, very fine droplets of lithium thus sprayed form a dispersion of liquid lithium onto which is conveyed a beam of protons in order to generate a neutron field. However, the expected yield for the production of neutrons on droplets is very low because of the small cross section of encounter between the proton beam and the lithium. Furthermore, the thermal power received by the droplets carries the risk of causing them to volatilize, especially since the free surface/volume ratio is greatly increased in this embodiment. Alternatively, [Ref. 3] describes a configuration, in which a fine layer of liquid lithium is supported at the periphery of the disk by a very thin (of the order of one micron thick) support foil, for example a beryllium foil, through which the proton beam can pass in order to interact with lithium. However, the removal of heat by conduction on such a thin foil is low, so a target rotating at high speed as disclosed in [Ref 3] will overheat and rapidly be destroyed. Furthermore, the forces exerted at the periphery on such a thin support foil cannot be withstood by and are not compatible with an adhesion system. Furthermore, the thin support foil described in [Ref. 3], in addition to being mechanically complicated to produce in durable form, leads to a loss of energy by the proton beam that has to pass through it and possibly to the generation of other secondary nuclear particles.

It is an objective of the present description to propose a new liquid target that allows the installation to be more compact and a reduced quantity of target material, notably for the generation of neutron fields, while at the same time allowing excellent heat removal.

SUMMARY OF THE INVENTION

A first aspect of the present description relates to a liquid target for the production of nuclear particles, comprising:
- a shell formed by a surface of revolution and mounted to rotate about an axis of rotation coincident with an axis of revolution of said shell;
- a reservoir containing a target material which in operation is in the liquid state, said target material being suited to the production of said nuclear particles;
- a target material raising device configured to entrain, in operation, the target material from the reservoir toward an upper surface of the shell;
- a gutter formed along an external perimeter of the shell and configured to receive, in operation, droplets derived from a film of target material induced by centrifugal action on said upper surface of the shell as the shell is rotated;
- at least one return pipe forming a fluidic connection between said gutter and said reservoir; and
- an inlet pipe configured, in operation, to let in a beam of accelerated particles into a zone of impingement of said accelerated particles with the shell, said zone of impingement being situated on said upper surface of the shell, the interaction of said accelerated particles with the target material circulating on said upper surface of the shell generating said nuclear particles.

A target according to the present description thus makes it possible, through centrifugal action, to obtain a film of target material in the liquid state, formed in a device operating in closed circulation. The result of this, notably in comparison with the liquid targets described in the prior art, is a reduction in the bulkiness of the installation required for operation of the target and a limiting of the volume of liquid required.

Furthermore, because the zone of impingement of the accelerated particles with the target, and more specifically with the shell, is a zone situated on the upper surface of the shell, a film of target material with which film the accelerated particles directly interact, is generated in the target according to the present description. The film of target material thus generated on the upper surface of the shell is thick enough that excellent heat removal is obtained both by conduction into the shell which supports it and by convection via the liquid; as a result it is possible without degradation to withstand high incident particle beam powers and to produce higher fluxes of nuclear particles.

The target according to the present description is able to operate, in use, in a "horizontal" configuration, namely with an axis of rotation of the shell arranged vertically. Such an arrangement allows the target material in the liquid state that is thrown out into the gutter to be reinjected directly into the reservoir under the effect of gravity without using additional energy.

What is meant by a "nuclear particle" is any particle that can be produced through a nuclear reaction, for example neutrons, protons, alpha particles.

What is meant by a "beam of accelerated particles" is, in the present description, particles, for example protons or deuterons, which, bombarded against a given target material, enable the production of nuclear particles.

According to one or more exemplary embodiments, the target material comprises fluids which, in operation and at very low temperatures, are in the liquid state, such as hydrogen, nitrogen, argon or xenon.

According to one or more exemplary embodiments, the target material comprises materials, for example lithium metal or fluorinated molten salts which, in operation and at high temperature, are in the liquid state.

Thus, according to one or more exemplary embodiments, the liquid target is suited to the generation of neutron fields and the target material is, for example, lithium metal which, in operation, is in the liquid state.

In the case of the production of neutrons, the target is generally surrounded by a neutron moderator; the compactness of the target according to the present description allows all of the lithium to be kept in a zone of thermal neutrons backscattered by the moderator that surrounds it. This means that the $^7$Be can be converted using the $^7$Be$(n_{th},p)^7$Li reaction, the product obtained being none other than the initial $^7$Li. This then gets around the need for a $^7$Be trap and auto regeneration of the liquid lithium is achieved.

According to one or more exemplary embodiments, notably in the case in which the target material contains lithium, the shell is made of molybdenum or of a molybdenum-based alloy (for example TZM which is based on molybdenum (99.5%) with zirconium and titanium) or of steel or of a combination of these two materials. In the case of the generation of types of particles other than neutrons, different materials may be used for the shell, the materials being selected so that they do not react with the target material in the liquid state at the temperature of use; for example, the shell may be made of carbon-based materials in the case of target materials containing fluorinated molten salts.

According to one or more exemplary embodiments, the surface of revolution forming said shell comprises at least a first conical truncated part the vertex of which is situated on the axis of rotation and which has a given vertex half-angle. Other shapes may be envisioned for said first part, such as, for example, a shape exhibiting a curved profile in a meridian plane (or plane containing the axis of revolution).

According to one or more exemplary embodiments, in the case of the use of a first conical truncated part, the vertex half-angle of said conical truncated part is comprised between 0° and 90°, advantageously between 40° and 50°.

In the present description, a radius r of the first part (for example conical truncated or curved part) at a given point is defined in the plane perpendicular to the axis of rotation of the shell, by a distance between said axis of rotation and said point.

According to one or more exemplary embodiments, a radius of the first part at the zone of impingement is comprised between 15 cm and 45 cm.

According to one or more exemplary embodiments, the surface of revolution forming said shell comprises at least a first part and a second part forming a base to which said first part is connected. For example, the base is flat or conical truncated.

According to one or more exemplary embodiments, the first part is connected to said base by a fillet radius ensuring a continuous variation in gradient between said base and said first part; that makes it possible to ensure that the upper surface of the shell on which, in operation, the liquid target material spreads out, does not include a connection that could distort the flow of the liquid. For example, a radius of curvature of the fillet radius is comprised between 5 mm and 50 mm.

According to one or more exemplary embodiments, said first part and said base are of one piece. Alternatively, said first part and said base may be formed of two parts assembled by screwing or welding.

According to one or more exemplary embodiments, the target material raising device comprises one or more vanes or a rotor, configured to be driven in rotation about an axis integral with the axis of rotation of the shell. The rotating of the shell causes the liquid to circulate because of the effect of centrifugal action as soon as the liquid has been raised up to the upper surface of the shell, without requiring any other mechanism for pumping the liquid.

According to one or more exemplary embodiments, said system for raising the target material comprises a pump interposed between one end of the return pipe and the reservoir. This device is more complex but does however make it possible to eliminate the correlation between flow rate and rotational speed.

According to one or more exemplary embodiments, the target further comprises a plate arranged above the shell, said plate notably making it possible to limit the total surface area of liquid in direct communication with the vacuum in the vicinity of the beam inlet zone. Said plate may be fixed, or rotary and secured to the shell.

According to one or more exemplary embodiments, the target further comprises a fixed upper casing arranged to at least partially encase said upper surface of the shell. According to one or more exemplary embodiments, the target further comprises a fixed lower casing arranged to at least partially encase a lower surface of the shell opposite to said upper surface.

According to one or more exemplary embodiments, said lower casing is secured to said reservoir.

Said upper and/or lower casings allow vapors originating from the target material in the liquid state to be confined and condensed on their walls.

According to one or more exemplary embodiments, said upper casing is traversed by said inlet pipe configured to let in said beam of accelerated particles into said zone of impingement.

According to one or more exemplary embodiments, said upper casing comprises one or more openings for pumping the target material in the liquid state and/or for the passage of a device for driving the rotation of the shell if the latter is driven from above, namely from the side of the upper surface of the shell.

According to one or more exemplary embodiments, the gutter is secured to said upper casing and is formed in such a way as to surround said external perimeter of the shell and to curl under the lower surface of the shell, opposite to said upper surface.

According to one or more exemplary embodiments, said upper and lower casings are connected, at least locally, by means of said gutter.

According to one or more exemplary embodiments, the reservoir comprises an opening for the passage of a device for driving the rotation of the shell if the latter is driven from below, namely from the side of the lower surface of the shell, opposite to the upper surface. Said opening is then arranged to allow fluid-tight passage of the drive device.

According to one or more exemplary embodiments, the reservoir and/or the upper and/or lower casings are formed from a material containing molybdenum, stainless steel, or a combination of the two materials.

According to one or more exemplary embodiments, the target comprises a plurality of return pipes between the gutter and the reservoir, for example between 2 and 8 pipes. The return pipe or pipes may have various shapes (circular, ovoid, etc. cross sections) and variable cross-sectional areas.

According to one or more exemplary embodiments, the target is configured to accept a stable rate of rotation of the shell at a speed comprised between 300 and 800 revolutions/min.

The total volume of target material in the liquid state in a target according to the present description is determined according to the geometry of the system and to the nominal rotational speed chosen for operation. According to one or more exemplary embodiments, the volume of liquid in the closed-circulation system is comprised between 2 and 5 liters, which is to say a volume almost three times lower than the volume of liquid required in targets based on liquid lithium known from the prior art. According to one or more exemplary embodiments, the target is configured to produce, in operation, a film of target material in the liquid state of a thickness comprised between 50 µm and 5 mm. Advantageously, in the case of liquid lithium, a thickness comprised between 80 µm and 140 µm, for example between 80 µm and 100 µm will be chosen as that allows the maximum energy loss, and therefore maximum heating, to be situated in the surface zone of the shell rather than in the film of liquid lithium. Furthermore, excessively small thicknesses of lithium carry the risk of leading to localized dewetting of the lithium on the surface of the shell. According to one or more exemplary embodiments, the inlet pipe for the beam of particles is arranged in a plane containing the axis of rotation of the shell. This configuration corresponds to minimum deformation of the shape of the zone of impingement of the beam with respect to the cross section of this beam.

According to one or more exemplary embodiments, the inlet pipe for the beam of particles is arranged in a plane tangential to a circumference of rotation at the zone of impingement. This configuration corresponds to significant deformation of the zone of impingement of the beam with respect to the cross section of this beam.

In general, there is a great deal of latitude in the choice of the angles defining the orientation of the inlet pipe with respect to the zone of impingement and these angles may be chosen in order to minimize the time of residence of the target material in the liquid state beneath the beam of accelerated particles.

According to one or more exemplary embodiments, the inlet pipe for the beam of accelerated particles is equipped with a system for rapidly shutting off the beam.

According to one or more exemplary embodiments, the inlet pipe for the beam of accelerated particles is equipped with a condenser.

According to one or more exemplary embodiments, the target further comprises a device for preheating the target material in the reservoir.

According to one or more exemplary embodiments, the target further comprises a device for preheating at least part of the upper casing and/or the lower casing and/or of the reservoir.

According to one or more exemplary embodiments, the target further comprises a cooling system.

According to one or more exemplary embodiments, the target further comprises a chamber configured to create, in the region of the zone of impingement, a vacuum compatible with the generation of said nuclear particles.

A second aspect of the present description relates to a system for producing nuclear particles, comprising:
  a source of particles suited to producing, upon interaction with a target material, said nuclear particles,
  a particle accelerator configured to receive a beam of particles from said source and to form a beam of accelerated particles,
  a target according to the first aspect comprising said target material and configured to receive, at the inlet pipe, said beam of accelerated particles and to generate, at said zone of impingement, said nuclear particles.

According to one or more exemplary embodiments, in the case of the generation of a neutron field, the production system further comprises a neutron moderator arranged around the target.

According to one or more exemplary embodiments, the source of particles emits protons or deuterons.

A third aspect of the present description relates to a method for producing nuclear particles by means of a production system according to the second aspect. According to one or more exemplary embodiments, said method comprises:
rotating said shell,
circulating the liquid by operating the raising device;
admitting the beam of accelerated particles originating from said particle accelerator into said inlet pipe.

According to one or more exemplary embodiments, the method further comprises, in the case of target materials that are solid at ordinary temperature, a step of preheating the reservoir containing the target material and/or various elements of the target. The preheating step then allows the liquid to be circulated even in the absence of the thermal power transmitted by the beam of accelerated particles, in the case of a target material that is solid at ordinary temperature. In the case of low-temperature fluids, the method may alternatively comprise a regulation of the cooling.

According to one or more exemplary embodiments, the method further comprises the cooling of the target in the presence of the beam of accelerated particles, with a progressive stopping of the preheating, correlating to the thermal power transmitted to the system thereby.

According to one or more exemplary embodiments, the rotational speed of the shell is comprised between 300 and 800 revolutions/min.

According to one or more exemplary embodiments, the speed of the ascending flow of the liquid on said upper surface of the shell is comprised between 1 m/s and 3 m/s. The ascending speed is defined as the speed of travel of the liquid film relative to the shell.

According to one or more exemplary embodiments, the tangential speed of the liquid in the zone of impingement is comprised between 5 m/s and 40 m/s.

BRIEF DESCRIPTION OF THE FIGURES

Further advantages and features of the invention will become apparent from reading the description which is illustrated by the following figures:

FIG. 4 depicts a diagram illustrating an example of a liquid target according to the present description.

DETAILED DESCRIPTION OF THE INVENTION

Figure 1:
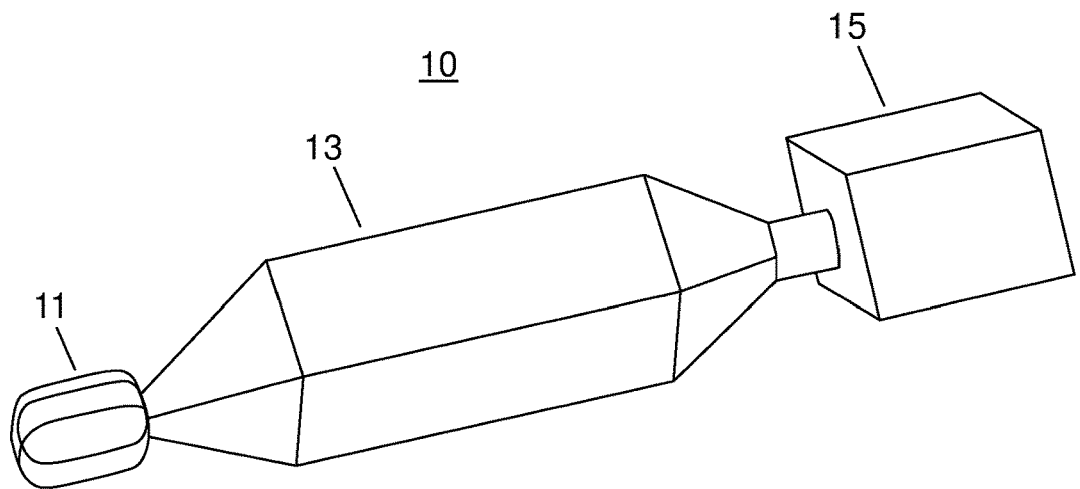
FIG. 1 schematically depicts one example of a system for generating nuclear particles according to the present description.

FIG. 1 illustrates in general terms the elements of a system 10 for producing nuclear particles according to the present description. The system 10 comprises a particle source 11, for example a source of protons or a source of deuterons, a particle accelerator 13 to form, from the particles emitted by the source 11, a beam of accelerated particles, and a target 15, the target 15 allowing, in operation, the interaction between the beam of accelerated particles and a film of target material in the liquid state to generate the nuclear particles. The target is moreover arranged inside a vacuum chamber (not depicted) compatible with the vacuum levels required for the beams of particles.

In the case, for example, of the generation of a neutron field, the target material may be lithium metal, in the liquid state for temperatures in excess of 180° C. The incident particles may, according to one example, be protons: a proton is collided with a lithium nucleus ($^7$Li) to form, by means of a nuclear reaction, a beryllium nucleus ($^7$Be) with the ejection of a neutron having energy comprised between 25 keV and 785 keV.

According to another example, the incident particles are deuterons: a deuteron is collided with a lithium nucleus ($^7$Li) to form, by means of a nuclear reaction, two $^4$He nuclei.

When the neutron field is generated using lithium, the system 10 may moreover comprise, all around the target 15, a moderator medium (not depicted) in order to diminish the energy of the neutrons of the neutron field thus generated. The moderator for example comprises a hydrogenated medium (polyethylene or the like). The moderator slows the neutrons allowing them to be backscattered toward the target 15. In this way, these neutrons will interact with the $^7$Be, the product of the $^7$Li(p,n)$^7$Be reaction. By capturing a slow neutron with a very high effective cross section, the $^7$Be is converted into $^7$Li according to the $^7$Be($n_{th}$,p)$^7$Li reaction. The product obtained is none other than the initial $^7$Li, which therefore corresponds to auto regeneration of the lithium. This then makes it possible to dispense with the need for a $^7$Be trap and thus eliminates the radiological risk.

Figure 2:
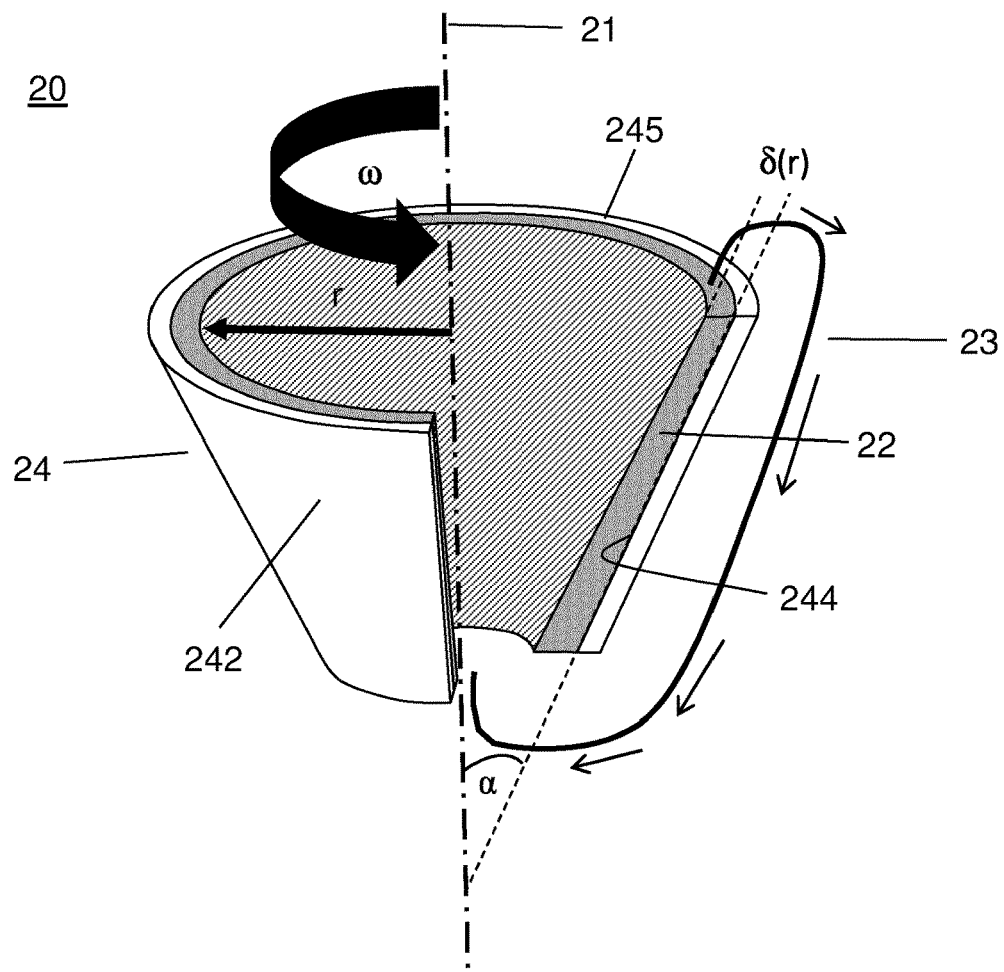
FIG. 2 depicts a diagram illustrating the principle of a liquid target according to the present description.

FIG. 2 is a diagram illustrating the principle of operation of a liquid target 20 according to one example of the present description.

The target 20 schematically depicted comprises a shell 24 formed by a surface of revolution and mounted to rotate about an axis of rotation 21 coincident with an axis of revolution of said shell. In the example of FIG. 2, the shell comprises a conical truncated part 242 of which the vertex is situated on the axis of rotation and which has a given vertex half-angle $\alpha$.

The target 20 moreover comprises a reservoir (not depicted in FIG. 2) comprising a target material which is in the liquid state in operation, for example lithium, and a device for raising the target material (this device is not depicted in FIG. 2) which is configured to entrain, in operation, the target material in the liquid state from the reservoir toward the upper surface 244 of the rotating shell. An inlet pipe (not depicted in FIG. 2) allows a beam of accelerated particles to be, in operation, let in into a zone of impingement with the shell, the interaction of said accelerated particles with the target material circulating on said upper surface of the shell generating, by nuclear reaction, nuclear particles.

As illustrated in FIG. 2, the rotating of the shell 24 at a given angular velocity ω generates, through a centrifugal effect, on the upper surface of the shell, a film 22 of target material in the liquid state, for example liquid lithium, of thickness δ(r), r being a radius of the conical truncated part 242. Because of the centrifugal action, the film of liquid 22 experiences an upward movement along the conical truncated part 242 toward an external perimeter 245 of the shell, forming, in this example, an annular end, which results in liquid overspilling to the outside of the conical truncated part, in the form of a free film, of runs or of droplets. One or more return pipe(s) (not depicted in FIG. 2) then allow(s) the target material in the liquid state to be recovered and directed back toward the reservoir, for the purposes of allowing it to be recirculated in a closed system, depicted schematically by the reference 23 in FIG. 2.

In cases in which a neutron field is generated from lithium, the production of neutrons takes place in the first few microns of the subsurface of the metal; beyond that, the subsequent path of the beam corresponds only to a slowing of the protons, and therefore to a deposition of energy that it is desirable to minimize in lithium in order to limit the heating thereof. It has been shown (see Halfon et al. [Ref. 4]) that the penetration of the proton beam continues to a depth with maximum deposition of energy from 140 µm onwards. What is therefore sought is for the thickness of lithium in the zone of impingement with the beam of particles to be below a predetermined value so that a significant proportion of the energy is deposited not in the liquid but in the shell. Typically what is sought is a thickness of liquid lithium in the zone of impingement of less than 140 µm but which is thick enough not to stray into a range liable to lead to dewetting of the film as a result of local fluctuations. Advantageously, this thickness is comprised between 100 µtm and 140 µm.

In the example of FIG. 2, the profile of the shell is conical truncated. Other examples of profiles are described hereinafter (see FIGS. 3A and 3B). A shell profile involving a conical truncated part allows for an analytical calculation of the thickness of the film of liquid 22 as a function of parameters including: the vertex half-angle α of the conical truncated part, the rotational speed co of the shell, the radius r of the conical truncated part at the zone of impingement and the flow rate of the liquid. These calculations may be based on the publications by S. V. Kralshevsky et al. (Ref [5, 6]). In the particular case of targets with recirculation based on a raising system connected to the axis of rotation, the flow rate is not an independent parameter but is linked to the rotational speed of the shell.

Figure 3A:
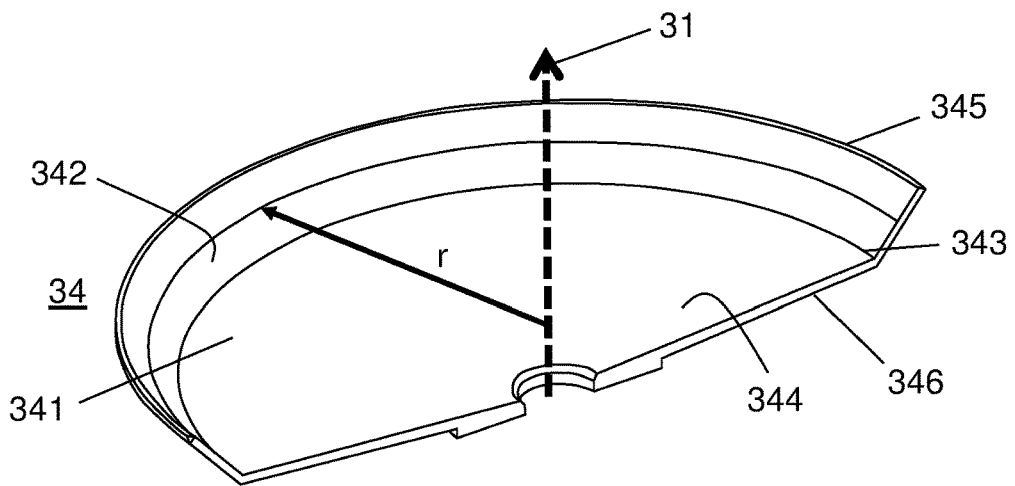
FIG. 3A depicts a diagram illustrating a first example of a shell in a target according to the present description.
Figure 3B:
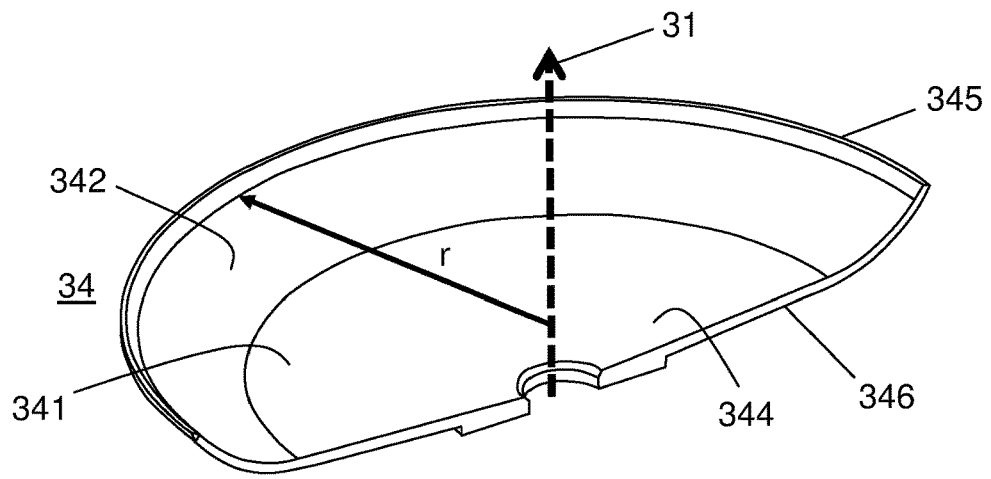
FIG. 3B depicts a diagram illustrating a second example of a shell in a target according to the present description

FIGS. 3A and 3B show two examples of parts of a shell 34 with different profiles in a meridian plane. In these examples, the shell comprises a first part 342 and a second part 341 forming a base to which the first part is connected. In both instances, in operation, the film of liquid (which is not depicted in FIGS. 3A, 3B) is formed on an upper surface 344 of the shell and, in operation, experiences an upward movement along the first part 342 toward an external perimeter 345 of the shell. The surface 346 opposite to the upper surface 344 is referred to as the lower surface of the shell. In the example of FIG. 3A, the first part 342 is conical truncated. The base 341 and the conical truncated part 342 are connected by a fillet radius 343 providing a gentle angular transition between these two parts in order to cause the least possible disruption to the flow of the liquid. The fillet radius 343 is characterized for example by a radius of curvature comprised between 5 mm and 50 mm.

The shell does not necessarily have to be made up of conical truncated elements and may be formed by a surface of revolution of which the curvature changes evenly, as depicted in FIG. 3B. Thus, in the example of FIG. 3B, the first part 342 has a curved part in a meridian plane containing the axis of revolution 31. In a target with a shell like the one depicted in FIG. 3B, an approximation of the thickness of the liquid film at the zone of impingement can be calculated using the results of the thickness calculations performed for the case of a conical truncated part and using, as the vertex half-angle α, a mean value for the values of the tangents to the shell in the zone of impingement.

FIG. 4 depicts a diagram illustrating a target 40 according to one example of the present description, for example, although not exclusively, a target based on liquid lithium.

The target 40 comprises an axisymmetric shell 34 rotating about an axis of rotation 31 with a conical truncated part 342 connected to a base 341, as in the example of FIG. 3A. The shell further comprises in this example a third part 440 forming a tubular extension dipping down in a reservoir 46 comprising a target material which is in the liquid state in operation. The shell is made from a material comprising, according to some embodiments, molybdenum and/or steel or a combination of these two materials.

In the example of FIG. 4, the target 40 further comprises a fixed upper casing 452, arranged so that it at least partially encases the upper surface 344 of the shell 34 on which, in operation, a film of target material in the liquid state will form. The upper casing 452 seeks to confine the vapors emanating from the liquid film formed, in operation, on the upper surface 344 of the shell.

In the example of FIG. 4, the target 40 further comprises a fixed lower casing 451 which encases the lower surface 346 of the shell 34 opposite to the upper surface 344 on which the liquid film is formed.

In the example of FIG. 4, a device for recovering target material in the liquid state comprises a gutter 457 arranged on the external perimeter 345 of the shell and configured to receive, in operation, droplets emanating from the film of target material which film is induced through centrifugal action, on the upper surface 344 of the shell. Thus, the liquid thrown out by centrifugal action on the liquid as a result of the rotating of the shell is collected in the gutter 457.

In the example of FIG. 4, the lower casing 451 and the upper casing 452 are connected via the gutter. Thus, in this example, the gutter 457 is secured to the upper casing 452; more specifically the gutter is formed in this example by bending over one end of the upper casing 452 so that it surrounds the external perimeter 345 and curls under the lower surface 344 of the shell.

The target 40 moreover comprises a reservoir 46 configured to contain, in operation, the target material in the liquid state.

In the example of FIG. 4, the reservoir 46 is formed by an outgrowth of the lower casing 451. Nevertheless, it is entirely conceivable for the reservoir 46 to be independent of the lower casing 451 and to be made of a different material with a connection situated in a zone 462 of connection between the reservoir and the lower casing. In normal operation, the intention will be for the level of the liquid not to reach the connecting zone 462 in case it is drawn up by the effect of the centrifugal action by the lower surface of the shell 346.

The assembly comprising the lower casing 451, the upper casing 452 and the reservoir 46 in this example forms a fixed casing 45. The casing 45 is made for example of stainless steel and/or of a molybdenum-based alloy.

A preheating device (not depicted in FIG. 4) may be provided at the reservoir 46 to preheat the target material before it comes into operation and interacts with the beam of accelerated particles. Preheating may be beneficial in the case of a target material such as lithium metal, which presents in the liquid state at temperatures higher than ambient temperatures.

The target 40 moreover comprises an inlet pipe 49 for a beam of accelerated particles 50. The inlet pipe is arranged on the perimeter of an opening 48 opening through the upper casing 452; by its orientation it defines the zone of impingement on the rotary shell, as will be explained by means of FIGS. 6A-6C. The shape of the incident beam is defined upstream at the accelerator 13 (FIG. 1). In the example of FIG. 4, the casing 45 and the inlet pipe 49 are secured to one another.

In some embodiments, a window (not depicted in FIG. 4) may be used to separate the vacuum in the zone of impingement and the atmosphere of the target. Such a window is possible for example in cases in which the energy of the beam so permits (can be transmitted sufficiently through the window). In other exemplary embodiments, for example in the case of lithium targets for low-energy applications, transmission through a window would be insufficient and the inlet pipe 49 for the beam of particles may be equipped with a quick shut-off system and/or with a condenser (not depicted in FIG. 4).

The target 40 moreover comprises a raising device 47 for raising the liquid of the reservoir 46 toward the upper surface 344 of the shell 34.

In the example of FIG. 4, the raising device 47 is inserted partially or completely in the tubular continuation 440 of the shell 34 dipping down into the reservoir. The continuation 440 rotates as one with the shell and the raising system. The continuation 440 may be surrounded by a fixed tube, not depicted in FIG. 4, able to limit the spread of the rotational movement of the tubular continuation 440 of the shell 34 and of the raising system, to the entirety of the liquid in the reservoir.

In the example of FIG. 4, the raising device 47 is secured to the continuation 440 and is depicted in the form of an endless screw to symbolize the raising action. The raising device for example comprises a system of vanes 471 or an adapted version of a centrifugal rotor. In this way, the rotating of the shell automatically leads to the raising of the target material in the liquid state.

The gutter 457 is connected to the reservoir 46 by at least one return pipe 43 forming a fluidic connection between the two elements. Thus, the target material in the liquid state that is thrown out into the gutter is reinjected directly into the reservoir 46 under the effect of gravity without using additional energy to achieve this.

Several return pipes 43 make the flows inside the reservoir symmetrical. In the example of FIG. 4, there are, for example, four return pipes 43 situated at 90° from one another. Nevertheless, the number of return pipes 43, their respective sizes and their positions may evolve without changing the subject matter of the present description. The systems for supporting and stiffening the whole (the shell, liquid return pipes and casings) have not been depicted.

In addition to the aforementioned elements, the target 40 may comprise a plate 459 arranged above the shell. The plate 459 notably makes it possible to limit the total surface area of liquid that is in direct communication with the vacuum in the vicinity of the beam inlet zone. Said plate may be fixed, or rotary in this case secured to the shell.

The target 40 may also comprise one or more preheating and/or cooling devices, for example at the casings and the return pipe 43, depending on the target material employed and/or one or more condensation devices, for example for condensing lithium vapors.

In operation, the raising device 47 conveys the target material in the liquid state, for example liquid lithium, to the center of the shell 34 so as to form a film of liquid as explained by means of FIG. 2. The rotating of the shell 34 at an angular velocity ω spreads the liquid film through a centrifugal effect. The liquid film therefore flows from the center toward the outside of the conical truncated part 342 after a rotating of the shell 34.

The film thus formed spreads over the entirety of the upper surface 344 of the shell 34. The spinning causes the film to spread right out to the external perimeter 345 of the shell 34 and to be thrown out into the gutter 457. The liquid thrown into the gutter is directly reinjected into the reservoir under the effect of gravity by means of the return pipes 43 without using additional energy.

The target 40 incorporated into a generation system 10 as described for example by means of FIG. 1 allows implementation of a method for producing nuclear particles, for example for generating a neutron field in the case of using lithium as target material.

According to some exemplary embodiments, the method comprises a preliminary step of obtaining a vacuum of sufficient quality around the target 40, by means of the vacuum chamber 42, then the rotating of the shell 34 and of the raising device 47 to form the film of liquid (22, FIG. 2). The beam of accelerated particles 50 coming from the particle accelerator 13 is then admitted into the inlet pipe 49. The method may also comprise a preliminary step of preheating the reservoir 46 and/or parts of the casing 45 and of the return pipe 43.

Figure 5:
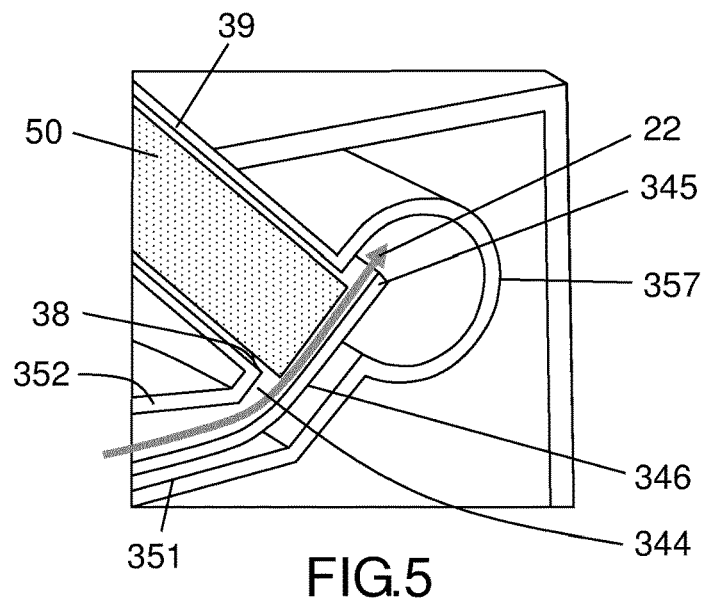
FIG. 5 depicts a diagram showing the circulation of the liquid in the example of target illustrated in FIG. 4.

FIG. 5 depicts a diagram showing in greater detail the circulation of the liquid in the example of target illustrated in FIG. 4 with the film 22 passing under the beam zone and subsequent recovery of the fluid by the gutter 457. Depending on the conditions employed (geometries and rotational speeds) the film may remain intact after it separates from the support shell or else may break up into runs or droplets.

Figure 6A:
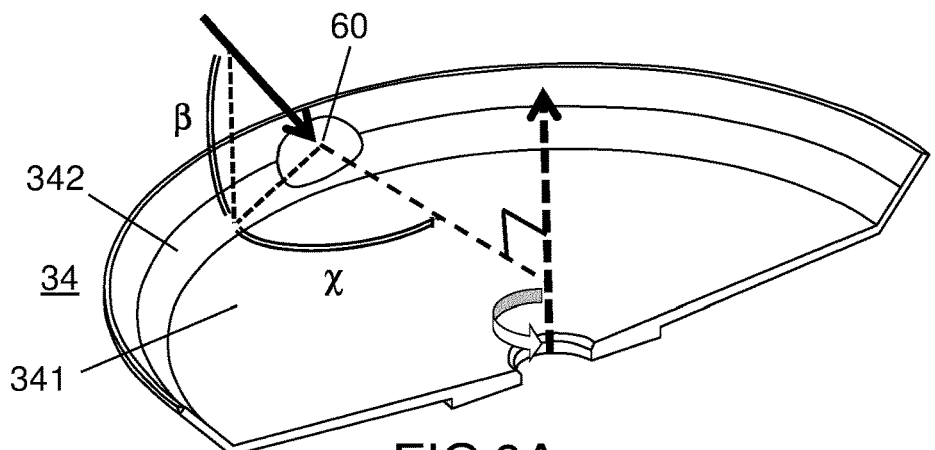
FIG. 6A depicts a diagram describing the angular referencing ($\beta$ and $\chi$) of the position of the inlet of the beam of particles with respect to the axis of rotation of the shell.
Figure 6B:
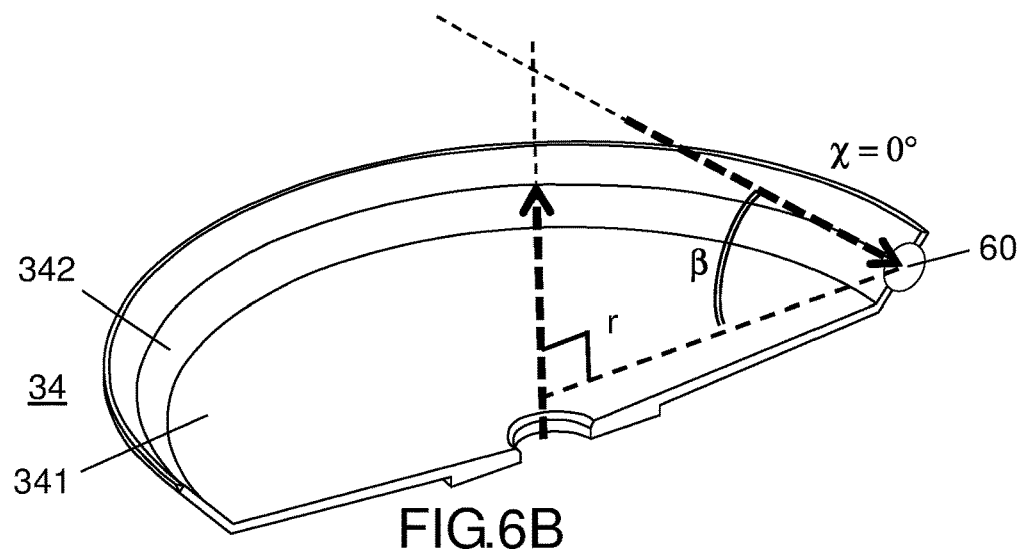
FIG. 6B depicts the special case in which the inlet pipe for the beam of particles is arranged in a plane containing the axis of rotation ($\chi=0°$).
Figure 6C:
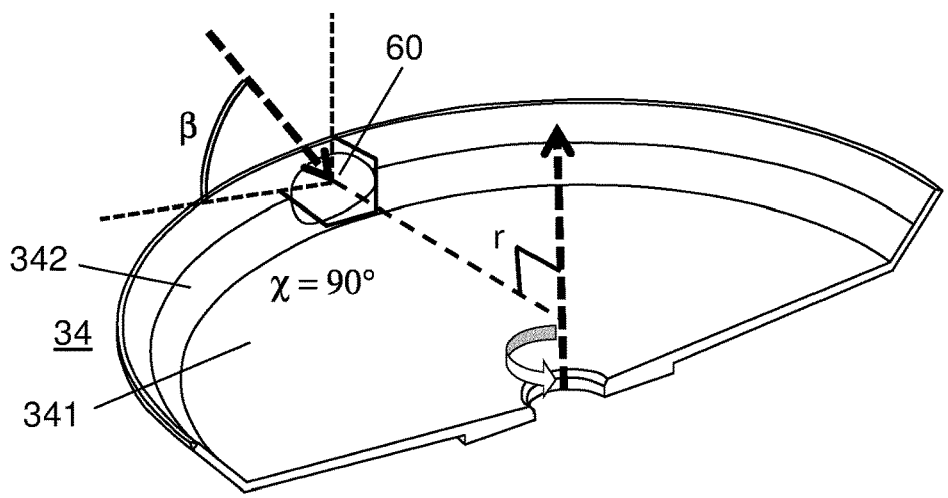
FIG. 6C depicts the special case in which the inlet pipe for the beam of particles is arranged in a plane tangential to a rotation circumference ($\chi=90°$).

FIGS. 6A to 6C more specifically illustrate the shape of the zone of impingement of the beam in various configurations of the inlet pipe.

As illustrated in FIG. 6A, the inlet pipe for the beam of particles is arranged in such a way that the beam of accelerated particles (which is indicated by an emboldened arrow in FIGS. 6A to 6C) is incident in a direction in the space that is identified by the angles β and χ.

According to one exemplary embodiment, the inlet pipe for the beam of particles is arranged in such a way that the beam of accelerated particles is incident in a plane containing the axis of rotation ($\chi = 0°$) as depicted in FIG. 6B. This configuration corresponds to minimum deformation of the zone of impingement of the beam compared with the cross section of this beam.

According to another exemplary embodiment, the inlet pipe for the beam of particles is arranged in such a way that the beam of accelerated particles is incident in a plane tangential to a circumference of rotation of radius r ($\chi = 90°$) as depicted in FIG. 6C. This configuration corresponds to significant deformation of the zone of impingement of the beam compared with the cross section of this beam.

There is a great deal of latitude in the choice of the angles (β and χ), according to the choice for the position of the rotational-drive system, of the liquid used, of the operating temperature and of the configuration of the particle accelerator upstream. In the case of liquid lithium, the values are advantageously selected in the range α<β<90° and 45°<χ<90° so that the time of residence of the lithium under the beam is minimized.

Although it has been described through a certain number of exemplary embodiments, the target for generating nuclear particles according to the present description has numerous variants, modifications and refinements which will be obvious to a person skilled in the art with the understanding that these different variants, modifications and refinements form part of the scope of the invention as defined by the claims which follow.

REFERENCES

Ref 1. Halfon et al. "*Demonstration of a high-intensity neutron source based on a liquid-lithium target for Accelerator based Boron Neutron Capture Therapy*" Applied Radiation and Isotopes 106 (2015) pp 57-62.

Ref 2. Kobayashi et al. "*Development of Liquid-Lithium Target of 7Li(p,n)7Be Reactions for BNCT*" Applied Radiation and Isotopes Volume 88 (2014) pp 198-202.

Ref. 3: U.S. Pat. No. 5,870,447

Ref 4. Halfon et al. "*High power liquid-lithium jet target for neutron production*" Review of Scientific Instruments 84, 123507 (2013).

Ref 5. Makarytchev et al. "*On modeling fluid over a rotating conical surface*" Chemical Engineering Science, vol. 52, no 6, pp 1055-1057 (1997).

Ref 6. Makarytchev et al. "*Thickness and velocity of wavy liquid films on rotating conical surfaces*" Chemical Engineering Science, vol. 56, pp 77-87 (2001)

The invention claimed is:

1. A target for the production of nuclear particles, comprising:
   a shell configured to rotate about an axis of rotation;
   a reservoir containing a target material which in operation is in the liquid state, said target material being suitable for the production of said nuclear particles;
   a target material raising device configured to entrain, in operation, the target material from the reservoir toward an upper surface of the shell;
   a gutter formed along an external perimeter of the shell and configured to receive, in operation, droplets from a film of the target material induced by centrifugal action on said upper surface of the shell as the shell is rotated;
   at least one return pipe forming a fluidic connection between said gutter and said reservoir;
   an inlet pipe configured, in operation, to let in a beam of accelerated particles into a zone of impingement of said accelerated particles with the shell, said zone of impingement being situated on said upper surface of the shell, on which is generated the film of target material, a direct interaction of said accelerated particles with the film of the target material on said upper surface of the shell generating said nuclear particles; and
   a fixed upper casing configured to at least partially encase said upper surface of the shell, said upper casing being traversed by said inlet pipe, wherein the gutter is secured to said upper casing and surrounds said external perimeter of the shell and curls under a lower surface of the shell, opposite to said upper surface of the shell.

2. The target as claimed in claim 1, further comprising a fixed lower casing arranged to at least partially encase the lower surface of the shell opposite to said upper surface, said lower casing being secured to said reservoir.

3. The target as claimed in claim 1, wherein said shell comprises at least a first part with variable curvature in a meridian plane containing the axis of revolution.

4. The target as claimed in claim 1, further comprising a chamber configured to create, in the region of the zone of impingement, a vacuum compatible with the generation of said nuclear particles.

5. A target for the production of nuclear particles, comprising:
   a shell configured to rotate about an axis of rotation;
   a reservoir containing a target material which in operation is in the liquid state, said target material being suitable for the production of said nuclear particles;
   a target material raising device configured to entrain, in operation, the target material from the reservoir toward an upper surface of the shell;
   a gutter formed along an external perimeter of the shell and configured to receive, in operation, droplets from a film of the target material induced by centrifugal action on said upper surface of the shell as the shell is rotated;
   at least one return pipe forming a fluidic connection between said gutter and said reservoir; and
   an inlet pipe configured, in operation, to let in a beam of accelerated particles into a zone of impingement of said accelerated particles with the shell, said zone of impingement being situated on said upper surface of the shell, on which is generated the film of target material, a direct interaction of said accelerated particles with the film of the target material on said upper surface of the shell generating said nuclear particles,
   wherein the target material raising device comprises one or more vanes or a centrifugal rotor, configured to be driven in rotation about an axis integral with the axis of rotation of the shell.

6. A target for the production of nuclear particles, comprising:
   a shell configured to rotate about an axis of rotation;
   a reservoir containing a target material which in operation is in the liquid state, said target material being suitable for the production of said nuclear particles;
   a target material raising device configured to entrain, in operation, the target material from the reservoir toward an upper surface of the shell;
   a gutter formed along an external perimeter of the shell and configured to receive, in operation, droplets from a film of the target material induced by centrifugal action on said upper surface of the shell as the shell is rotated;
   at least one return pipe forming a fluidic connection between said gutter and said reservoir; and
   an inlet pipe configured, in operation, to let in a beam of accelerated particles into a zone of impingement of said accelerated particles with the shell, said zone of impingement being situated on said upper surface of the shell, on which is generated the film of target material, a direct interaction of said accelerated particles with the film of the target material on said upper surface of the shell generating said nuclear particles,
   wherein said shell comprises at least a first conical truncated part whose vertex is situated on the axis of rotation and which has a given vertex half-angle (a), wherein the vertex half-angle (a) is between 40° and 50°.

7. A target for the production of nuclear particles, comprising:
- a shell configured to rotate about an axis of rotation;
- a reservoir containing a target material which in operation is in the liquid state, said target material being suitable for the production of said nuclear particles;
- a target material raising device configured to entrain, in operation, the target material from the reservoir toward an upper surface of the shell;
- a gutter formed along an external perimeter of the shell and configured to receive, in operation, droplets from a film of the target material induced by centrifugal action on said upper surface of the shell as the shell is rotated;
- at least one return pipe forming a fluidic connection between said gutter and said reservoir; and
- an inlet pipe configured, in operation, to let in a beam of accelerated particles into a zone of impingement of said accelerated particles with the shell, said zone of impingement being situated on said upper surface of the shell, on which is generated the film of target material, a direct interaction of said accelerated particles with the film of the target material on said upper surface of the shell generating said nuclear particles,
- wherein the target material is lithium and the nuclear particles generated are neutrons,
- wherein a thickness of the film of lithium induced by centrifugal action is between 80 μm and 140 μm.

* * * * *